United States Patent [19]

Anderson

[11] Patent Number: 5,460,524

[45] Date of Patent: Oct. 24, 1995

[54] DEVICE AND METHOD FOR SALIVA SUCTION WITH TONGUE RETRACTOR AND BIT HANDLE

[76] Inventor: Ross W. Anderson, 628 Forest Ave., Plymouth, Mich. 48170

[21] Appl. No.: 264,903

[22] Filed: Jun. 24, 1994

[51] Int. Cl.⁶ .................................................. A61C 17/10
[52] U.S. Cl. ................................................................ 433/93
[58] Field of Search .................................... 433/91, 93, 94

[56] References Cited

U.S. PATENT DOCUMENTS

| | | | |
|---|---|---|---|
| 3,049,806 | 8/1962 | Cofresi | 32/33 |
| 4,215,984 | 8/1980 | Reichley | 433/93 |
| 4,259,067 | 2/1981 | Nelson | 433/93 |
| 4,260,378 | 4/1981 | O'Neil | 433/93 |
| 4,511,329 | 4/1985 | Diamond | 433/31 |
| 4,975,057 | 12/1990 | Dyfvermark | 433/93 |
| 5,037,298 | 8/1991 | Hickham | 433/93 |
| 5,152,686 | 10/1992 | Duggan et al. | 433/93 |

OTHER PUBLICATIONS

David Kanas, D.D.S.; "Denta Pops T.M. Dry Field Aspirator"; Amera Dent Inc. of Nevada; May 1993.

Primary Examiner—Nicholas D. Lucchesi

[57] ABSTRACT

A dental device for removing saliva and retracting the tongue comprising a retraction unit (22) having a tongue shield (28). A bite handle (30) is connected to the tongue shield (28) to stabilize the unit (22), and is held between the biting teeth. At least one tube holder (36) is secured to the tongue shield (28) adjacent to a rearmost molar tooth, and a suction tube (24) is attached to each tube holder (36). A Y-tube adapter (26) may be used to connect two suction tubes (24) with a single conventional fitting of the operatory suction system. A method for removing saliva and retracting the tongue within an oral cavity including retraction with a tongue shield (28), and stabilizing the tongue shield (28) with a bite handle (30). The method further includes removing saliva along a tube holder (36) secured to the tongue shield (28) adjacent to a rearmost molar tooth.

20 Claims, 4 Drawing Sheets

1

DEVICE AND METHOD FOR SALIVA SUCTION WITH TONGUE RETRACTOR AND BIT HANDLE

BACKGROUND—FIELD OF INVENTION

This invention relates to a dental device, specifically to an improved device and method for removing saliva while retracting the tongue away from the teeth.

BACKGROUND—DESCRIPTION OF PRIOR ART

Many dental procedures, such as the placement of acrylic composite restorations, require a dry operating field to be successfully completed. Typically during a dental procedure, the oral cavity is being continuously filled with fluids such as saliva, water, and blood which interfere with the procedure. Additionally, the soft tissues of the tongue and cheeks contract whenever the patient swallows, pushing fluids onto the tooth surfaces.

Conventional dental suction devices consist of various types of tubing which are connected to a conventional operatory suction system at one end, with the opposite end being used for removing oral fluids. These devices often have shields connected to the tubing to retract soft tissues such as the tongue and cheeks. In most cases, however, these devices cannot isolate more than two or three teeth at a time.

Other dental suction devices isolate a greater number of teeth, but involve many complicated parts. These devices are difficult to insert into the oral cavity, sometimes requiring intraoral assembly. Another disadvantage of the complicated devices is their incompatibility with the two preferred methods of infection control: heat sterilization and the use of disposable instruments. These devices are often made of plastic which could melt in a sterilization oven, and are too expensive to be discarded after one use.

Clear access to the dental operating field is needed for most dental procedures. The operating field often includes the biting surfaces of the molar teeth as well as the outside or facial surfaces of the molar teeth. Many of the conventional suction devices have bite blocks or suction tubes passing over the posterior teeth which obstruct access to the molars.

U.S. Pat. No. 3,049,806, which was issued Aug. 21, 1962 to R. Cofresi for a "Multiple Saliva Ejector", discloses a device for suctioning saliva from the oral cavity including a tubular member having inlet orifices on both sides of a set of teeth and an adjustable brace serving as a tongue depressor.

U.S. Pat. No. 4,259,067, which was issued Mar. 31, 1981 to D. Nelson for a "Combined Saliva Ejector, Tongue Retractor and Throat Protector", discloses a dental device for isolating a region of the mouth, and includes a frame to retain the device and a shield member to retract the tongue from the lower teeth.

U.S. Pat. No. 4,511,329, which was issued Aug. 16, 1985 to M. Diamond for a "Moisture Controlling Lingual Dental Mirror" discloses a dental instrument for viewing the lingual or inside surface of the teeth, for providing saliva suction, and for serving as a tongue retractor.

U.S. Pat. No. 4,975,057, which was issued Dec. 4, 1990 to U. Dyfvermark for a "Dental Appliance", discloses a bite block appliance with an aperture serving as an evacuation nozzle for saliva suction.

U.S. Pat. No. 5,037,298, which was issued Aug. 6, 1991 to J. Hickham for an "Apparatus and Improved Process for Removing Saliva While Retracting Cheeks and Lips", discloses an apparatus for ejecting saliva, and includes a pair of saliva ejectors connected to a tongue retractor, and a cheek retractor connected to a tongue retainer which is secured to the tongue retractor.

U.S. Pat. No. 5,152,686, which was issued Oct. 6, 1992 to C. Duggan et al for a "Dental Appliance", discloses an appliance for suctioning debris from the oral cavity, and includes a tongue stabilizer and a removable suction tube secured to a bite block.

The devices of U.S. Pat. Nos. 4,259,067; and 5,037,298 are composed of numerous complicated parts, making them difficult to assemble and insert into the oral cavity. Two of the prior-art devices, U.S. Pat. Nos. 3,049,806; and 5,037,298, do not have a method for propping open the biting teeth, which would offer greater access to the operating field. Several of the devices, including U.S. Pat. Nos. 4,259,067; 4,975,057; and 5,152,686, are able to isolate only one-half of the dental arch, precluding a full-arch, or bilateral, dental procedure.

Most of these prior-art devices do not provide clear access to the rearmost molar teeth. Some of these devices have a bite block which directly obstructs access to the molars, including the devices of U.S. Pat. Nos. 4,511,329; 4,975,057; and 5,152,686. The devices of U.S. Pat. Nos. 4,975,057; and 5,152,686, do not have a means of retracting the cheek from the rearmost molar areas.

OBJECTS AND ADVANTAGES

Accordingly, several objects and advantages of the device and method of the present invention are:

(a) to provide clear access to an operating field including the rearmost molar teeth;

(b) to provide retraction of the tongue away from the teeth;

(c) to provide a device which can be easily inserted into the oral cavity;

(d) to provide suction to one side of the dental arch or to both sides of the arch simultaneously;

(e) to provide a device which can be fabricated as an inexpensive, disposable instrument;

(f) to provide a device which can prop open the biting teeth to increase access to the operating field; and (g) to provide a device which can retract the cheeks away from the rearmost molar teeth.

Still further objects and advantages of the present invention will become apparent from the following description and drawings.

DETAILED DESCRIPTION OF A PREFERRED EMBODIMENT

Figure 1:
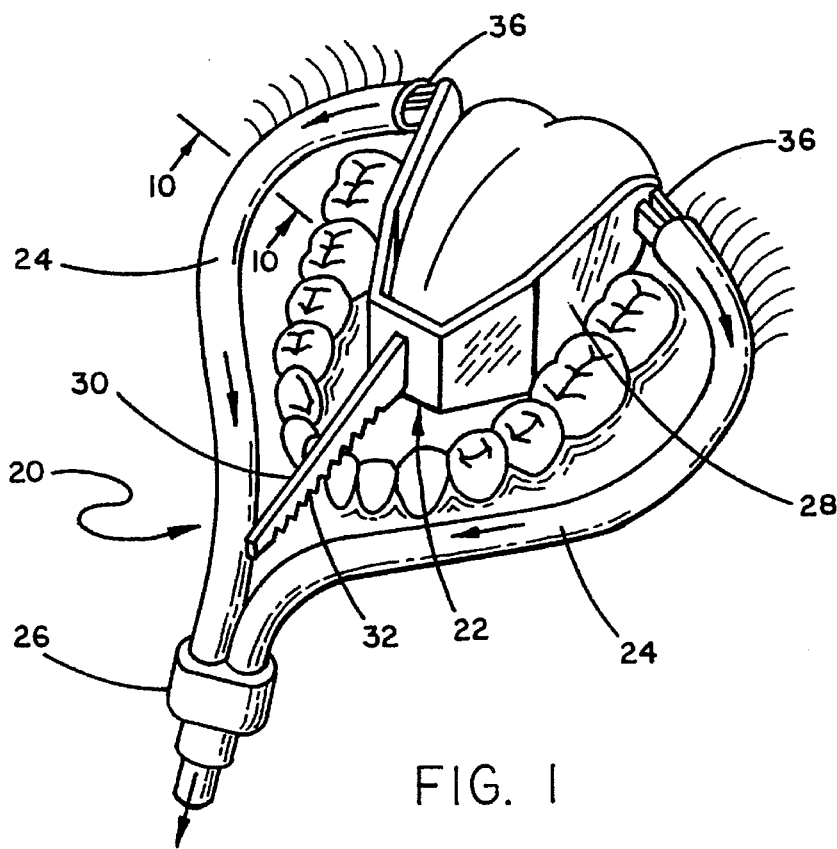
FIG. 1 is a perspective view of the preferred embodiment of the dental device positioned within the oral cavity.
Figure 2:
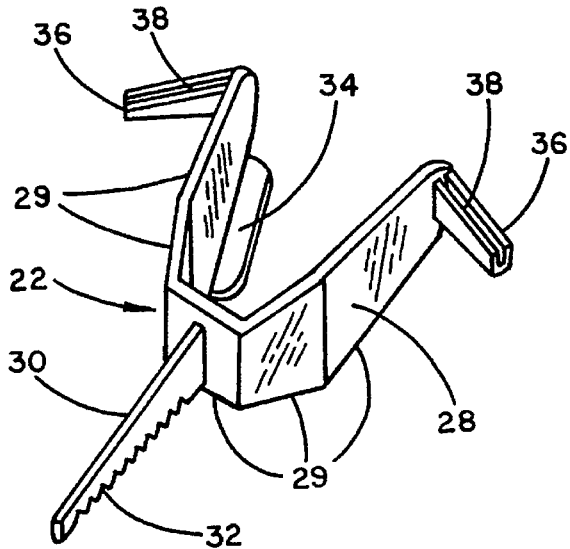
FIG. 2 is a perspective view of the preferred embodiment of a full-arch retraction unit.
Figure 3:
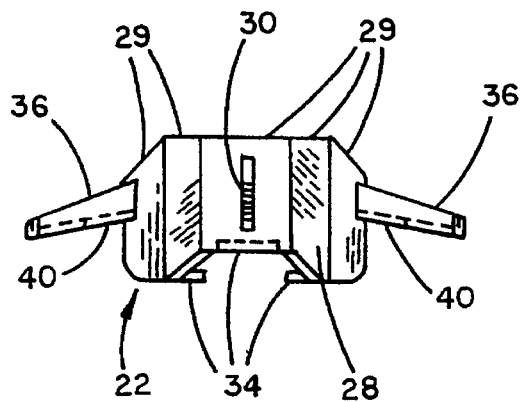
FIG. 3 is a front elevational view of the retraction unit.
Figure 4:
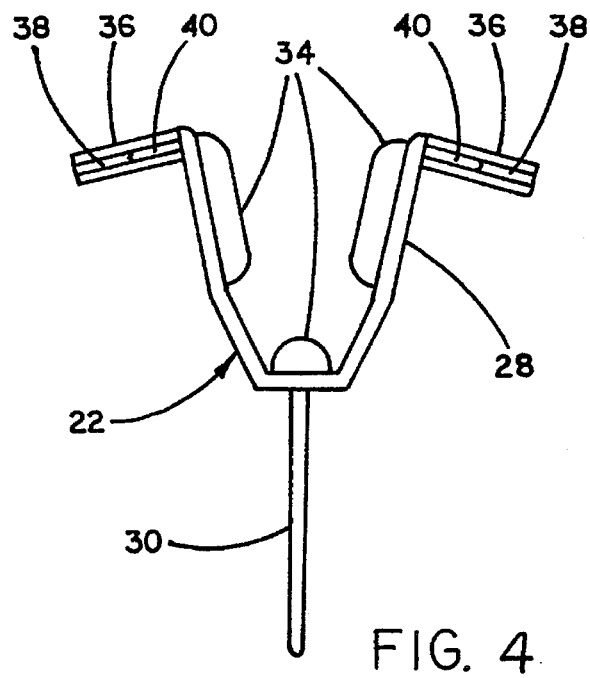
FIG. 4 is a top plan view of the retraction unit.
Figure 5:
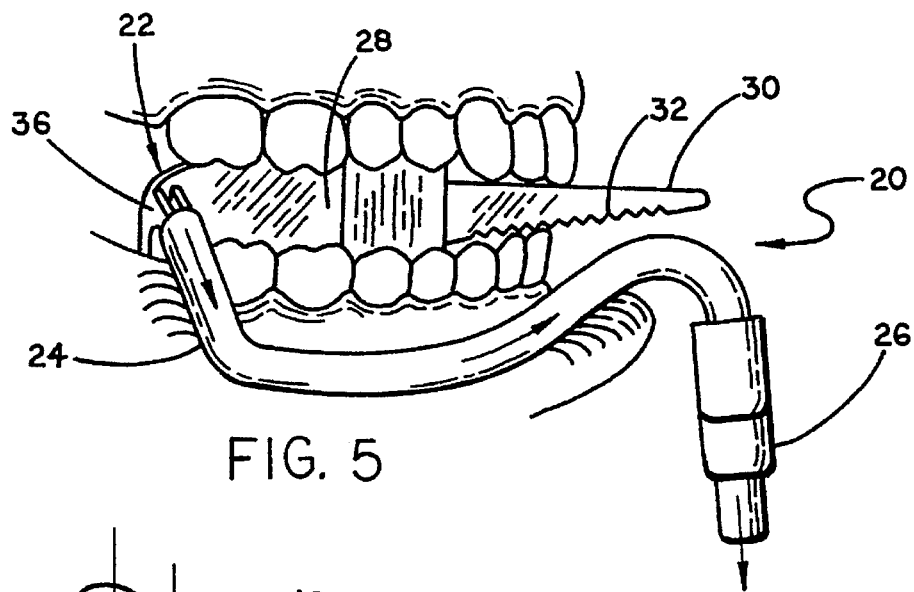
FIG. 5 is a side elevational view of the preferred embodiment of the device positioned within the oral cavity, and stabilized by the biting teeth.
Figure 6:
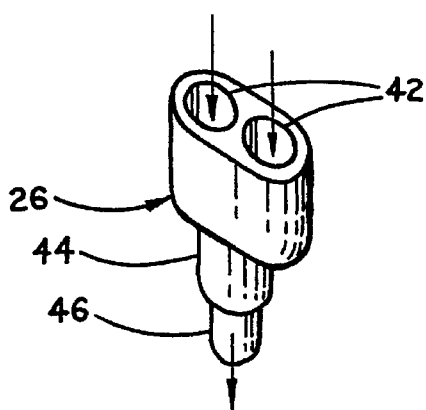
FIG. 6 is a perspective view of the Y-tube adapter.
Figure 7:
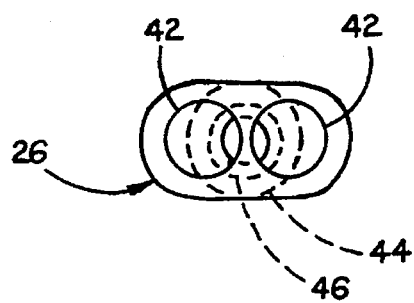
FIG. 7 is an enlarged top plan view of the Y-tube adapter.
Figure 8:
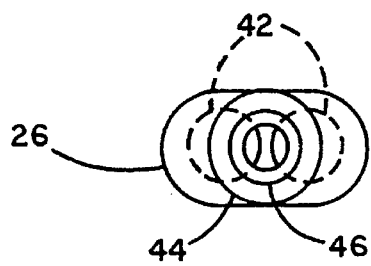
FIG. 8 is an enlarged bottom view of the Y-tube adapter.
Figure 9:
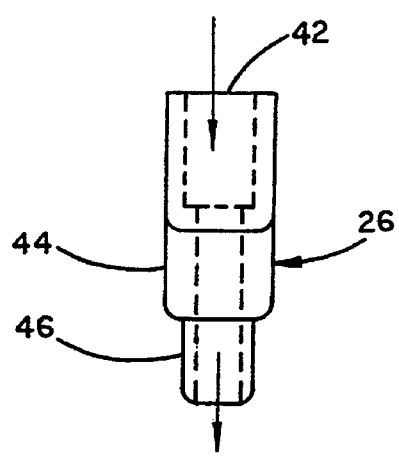
FIG. 9 is an enlarged side elevational view of the Y-tube adapter.

Referring now in detail to FIGS. 1–5, wherein like numerals represent like or similar parts throughout the several views, the preferred embodiment of the dental device of this invention is generally designated as 20. Dental device 20 serves to suction saliva and to retract the tongue and cheeks from the teeth within the oral cavity. Device 20 includes a full-arch retraction unit 22 attached to the posterior ends of a pair of saliva ejectors, or suction tubes 24—24. The anterior end of each suction tube 24 inserts into a Y-tube adapter 26, which in turn connects with a conventional dental operatory suction system (not shown). Retraction unit 22 has a bilateral, symmetrical design, making it suitable for isolating a full arch of teeth simultaneously.

Retraction unit 22 includes a tongue shield 28 having a generally U-shaped structure which retracts the tongue away from the teeth within the oral cavity. Tongue shield 28 preferably has a lateral width less than the inside width of a typical lower dental arch of teeth. The height of shield 28 is ideally greater than 15 mm in the posterior, with the anterior aspect tapering to a smaller height to avoid impingement of the lower gum tissue. The length of shield 28 is sufficiently long to pass rearward to a rearmost molar tooth when positioned within the oral cavity. The U-shaped structure of shield 28 is formed of five planar portions 29—29—29—29—29 secured to each other in series. This design, rather than a continuous curved structure, facilitates more efficient manufacturing with injection-molded materials.

A bite handle 30 is secured to the anterior portion of tongue shield 28. The length of bite handle 30 is preferably greater than 28 mm to allow further rearward positioning of tongue shield 28 within a large oral cavity having second or third permanent molars. Bite handle 30 is ideally composed of a sturdy material to withstand strong biting forces, and has a thickness of less than 2 mm, allowing the dental operator adequate visibility of the lower anterior teeth. Bite handle 30 preferably has a height of 3 to 6 mm, and has a series of notches 32 on its inferior surface which aid in securing handle 30 between the biting upper and lower teeth. Bite handle 30 stabilizes tongue shield 28 while retracting the tongue during a dental procedure. Additionally, bite handle 30 props open the biting teeth, thereby improving access to the biting surfaces of the teeth.

Three stabilizing shelves 34—34—34 are attached to the internal surface of tongue shield 28 and serve to hold retraction unit 22 downward and alongside the tongue. Retraction unit 22 further includes a pair of internal tube holders 36—36 which project laterally from the posterior edges of tongue shield 28. Tube holders 36—36 serve as attachment areas for the posterior ends of suction tubes 24—24. Holders 36—36 preferably have a length of 8 to 12 mm, and a thickness slightly larger than the inside diameter of suction tubes 24—24 to provide adequate frictional retention of tubes 24—24. The vertical thickness of tube holders 36—36 tapers down to a smaller dimension at the lateral ends, thereby allowing easier placement of tube 24 over holder 36. When retraction unit 22 is positioned within the oral cavity, tube holders 36—36 also function to hold suction tubes 24—24 rearward and lateral to the rearmost molar teeth. This rearward positioning of tube holders 36—36 prevents obstruction of access to the molar teeth by suction tubes 24—24.

A fluid channel 38 runs lengthwise within each tube holder 36 to facilitate saliva flow into suction tubes 24—24. A channel slot 40 penetrates a portion of each fluid channel 38 allowing greater saliva flow into fluid channel 38. When the operatory suction system is activated, saliva is ejected adjacent to tube holders 36—36 into suction tubes 24—24, then passing through Y-tube adapter 26 and onward into the conventional operatory suction system.

Suction tubes 24—24 pass behind and laterally to the molar teeth, and pass just medial to, or inside of, the cheeks. Thus, suction tubes 24—24 have the secondary function of retracting the cheeks away from the molar teeth, thereby increasing access and decreasing fluid contamination to the teeth. Each tube 24 then exits the oral cavity by passing over the lower lip of the oral cavity (see FIG. 5). The anterior end of each tube 24 inserts into Y-tube adapter 26 outside of the oral cavity.

Retraction unit 22 is preferably composed of a pliable, resilient material, allowing the two posterior edges of shield 28 to be bent towards each other. Bending shield 28 in such a manner brings tube holders 36—36 together, allowing easier insertion of device 20 into the oral cavity. After device 20 has been inserted into the oral cavity, it springs back to its original configuration.

Referring now to FIGS. 6–9, there are seen drawings for the illustration of a preferred embodiment of Y-tube adapter 26. Adapter 26 functions to connect both suction tubes 24—24 simultaneously with a conventional, female fitting of the operatory suction system (not shown). Two tube-holding inlets 42—42 receive the anterior ends of suction tubes 24—24 as illustrated in FIG. 1. A first male fitting, or high-volume attachment 44, fits into the conventional, female high-volume fitting of the operatory suction system (not shown). A second male fitting, or low-volume attachment 46, is secured in a concentric manner to high-volume attachment 44. Low-volume attachment 46 fits into the conventional, female low-volume fitting of the operatory suction system (not shown). Thus, adapter 26 has the ability to be connected with either of the two conventional sizes of fittings for the operatory suction system.

Figure 10:
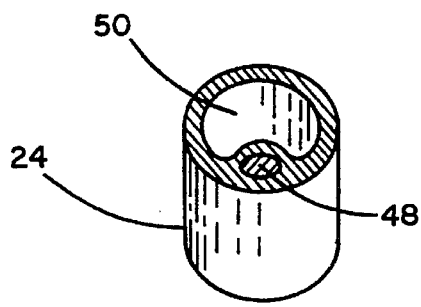
FIG. 10 is an enlarged sectional view of the suction tube, taken generally along line 10—10 of FIG. 1.

Referring now to FIG. 10, there is seen an enlarged sectional view of suction tube 24, taken generally along line 10—10 of FIG. 1. Embedded within the wall of tube 24 is a ductile wire, or wire reinforcement 48, which allows tube 24 to be formed into a curved or angled shape. Suction tube 24 is identical in diameter and composition to the tubing used in a conventional, low-volume, disposable saliva ejector (not shown). Conventional saliva ejectors are available from all major dental supply companies, and are used in virtually every dental office. The curvilinear length of suction tube 24 is roughly 140 to 180 mm. This allows the connection of tube 24 and Y-tube adapter 26 to lie comfortably outside of the oral cavity, well below the lower lip (see FIG. 5). Each tube 24 has a tube lumen 50, on its anterior and posterior ends. Tube lumen 50 of the posterior end of each tube 24 attaches over one of two internal tube holders 36—36, as illustrated in FIG. 1.

Figure 11:
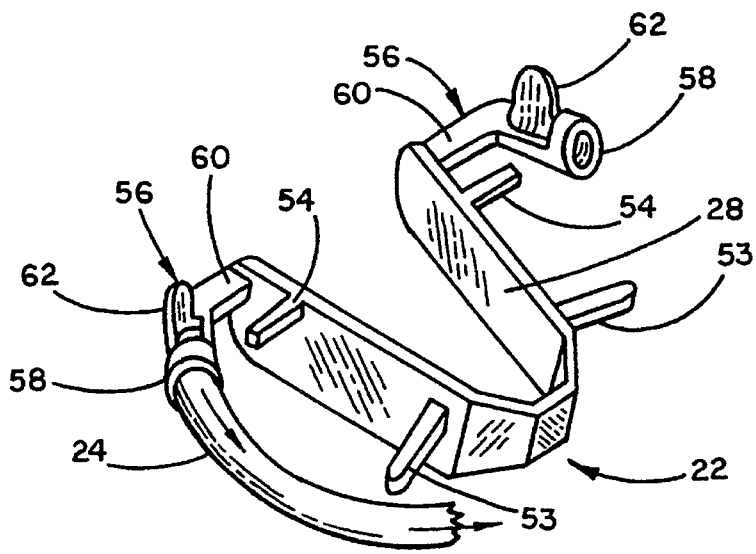
FIG. 11 is a perspective view of another embodiment of a full-arch retraction unit.

Referring now in detail to FIG. 11, there is seen another embodiment of full-arch retraction unit 22. A generally U-shaped tongue shield 28 gives attachment to a pair of posterior bite handles 53—53. Handles 53—53 preferably have a length of less than 15 mm to avoid obstructing access to the molar teeth, and have a height and thickness of about 3 mm. For illustrative purposes, only one suction tube 24 is shown in this drawing, although two such tubes 24 may be attached to unit 22. A pair of positioning fingers 54—54 is secured to the external surface of tongue shield 28. When unit 22 is positioned within the oral cavity, each positioning finger 54 contacts an upper molar tooth, thereby providing vertical stability to tongue shield 28. Each finger 54 has a thickness and width of less than 2 mm to avoid obstructing access to the biting surfaces of the molar teeth.

A pair of external tube holders 56—56 project laterally from the posterior areas of tongue shield 28. Tube holders 56—56 grip the external surface of each suction tube 24 by means of a tubular holding end 58. In this embodiment, each external tube holder 56 includes an extension arm 60 which serves to position suction tube 24 further laterally, away from the molar teeth. Each tube holder 56 further includes a retraction wing, or cheek retractor 62, which holds the cheek away from the rearmost molar teeth.

Figure 12:
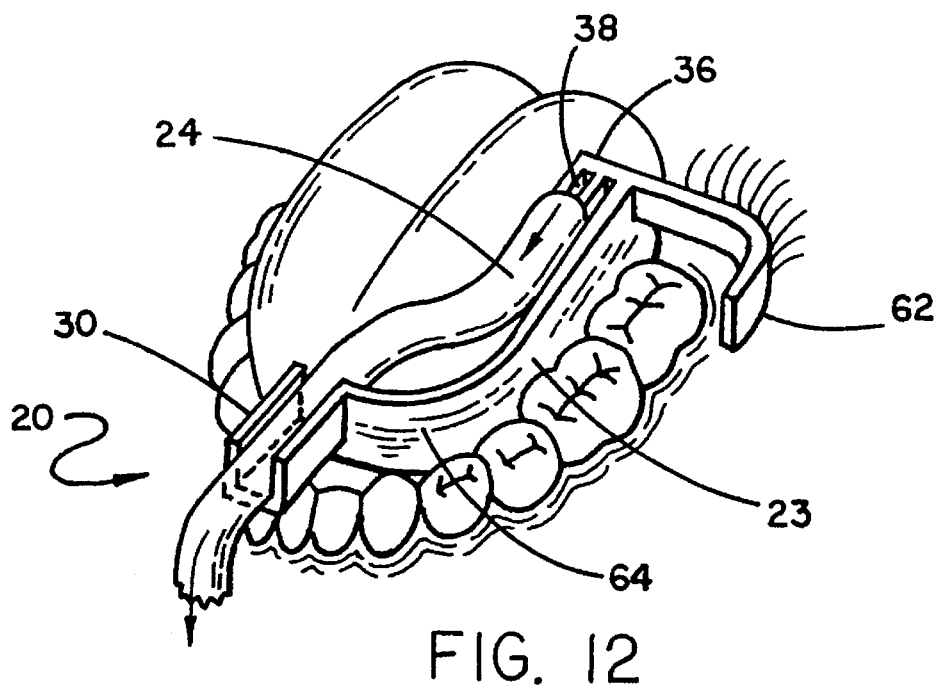
FIG. 12 is a perspective view of an embodiment of the dental device with a partial-arch retraction unit, positioned within the oral cavity.

Referring now in detail to FIG. 12, an additional embodiment of the dental device of this invention is generally designated as 20. There is seen a partial-arch retraction unit 64 including a generally arcuate tongue shield 28. Secured to the internal surface of shield 28 is an internal tube holder 36 which includes a fluid channel 38. A suction tube 24 is attached to holder 36. This embodiment would be used chiefly for unilateral dental procedures, and has the advantages of using only one suction tube 24 and avoiding the need for Y-tube adapter 26 (see FIG. 1). A trough-shaped bite handle 30 is secured to the anterior portion of tongue shield 28, and is held between the biting teeth when positioned within the oral cavity. A cheek retractor 62 is secured to the external surface of shield 28 to retract the soft cheek tissues from the molar teeth. In this embodiment, tube 24 is positioned along the internal surface of shield 28, passing through the trough of bite handle 30. This internal positioning of tube 24 allows even greater access to the side teeth and the rear molar teeth.

Figure 13:
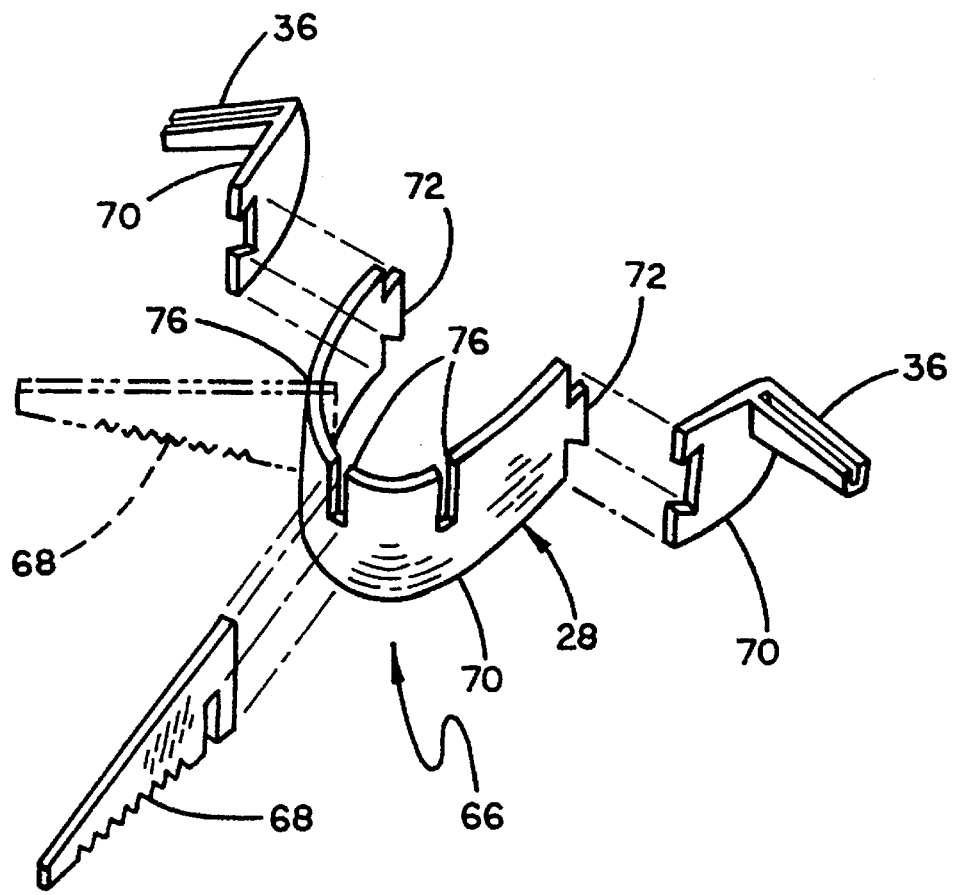
FIG. 13 is a perspective view of an embodiment of a retraction unit with a moveable bite handle.

Referring now in detail to FIG. 13 for an additional embodiment of the dental device, there is seen a full-arch adjustable retraction unit 66 including a generally U-shaped tongue shield 28. Shield 28 is made up of three detachable tongue-shield subunits 70—70—70, which join together at two snap-fit shield joints 72—72. Subunits 70—70—70 are detachable and reattachable, allowing for disassembly of shield 28 for more efficient packaging and shipping. Secured to the external surface of shield 28 are two internal tube holders 36—36. A moveable bite handle 68 is connected to shield 28 by one of three slot-shaped connectors, or handle attachments 76—76—76. Moveable bite handle 68 can be connected with any one of three handle attachments 76—76—76, thereby allowing greater access to one side or the other of the oral cavity. Bite handle 68 can also be removed temporarily to facilitate packaging and shipping.

SUMMARY, RAMIFICATIONS, AND SCOPE

Accordingly, the reader can see that the dental device and method of this invention are effective in maintaining a clear and dry operating field within the oral cavity. This is accomplished with a tongue retraction unit which has at least one bite handle serving to stabilize the unit against the tongue. The retraction unit also includes at least one tube holder positioned adjacent to the rearmost molar teeth. At least one suction tube is attached to the tube holders at one end, with the opposite ends connecting with a conventional operatory suction system. A Y-tube adapter may be used to connect two suction tubes with a single fitting of the conventional operatory suction system.

The present invention achieves a synergistic effect by simultaneously increasing access to the operating field and decreasing fluid contamination. This effect is created by: (1) providing at least one suction inlet adjacent to a rearmost molar tooth, (2) retracting the tongue from the teeth, and (3) stabilizing the retraction unit with an attached bite handle. This effect is enhanced by also retracting the cheek from the rear molar teeth. Additionally, in keeping with the trend towards sterile and disposable dental devices, the simple design of this device lends itself to fabrication with inexpensive, single-use materials.

There have been disclosed herein the best embodiments of the device of the present invention. However, it is to be understood that various changes and modifications may be made thereto without departing from the spirit of the invention.

What I claim is:

1. A dental device for removing saliva, and for retracting the tongue and cheek within an oral cavity, comprising a generally U-shaped tongue shield having an internal surface, an external surface, a first rear end, and a second rear end, for providing a wall between the tongue and the teeth, and for locating the tongue in a retracted tongue position; a bite handle connected to said external surface of said tongue shield in a position forward of said first rear end, projecting outward from said tongue shield, and engaged between the teeth when positioned within said oral cavity, for stabilizing said tongue shield against the tongue; a tube holder secured to said tongue shield generally adjacent to said first rear end, extending outward from said tongue shield, and located generally rearward to a rearmost molar when positioned within said oral cavity; a suction tube having an anterior end, a posterior end, and a tube wall, said posterior end attaching to said tube holder, for removing saliva from along a structural position of said tube holder, and for retracting the cheek from the teeth; and at least one reinforcement means carried within said tube wall of said suction tube, for providing said tube with sufficient strength to retract the cheek from the teeth.

2. The dental device of claim 1 further comprising a second tube holder; a second suction tube, having an anterior end, a posterior end, and a tube wall, said posterior end of said second suction tube attaching to said second tube holder; at least one reinforcement means carried within said tube wall of said second suction tube; and a Y-tube adapter comprising a first tube-holding inlet attached to said anterior end of said first suction tube, and a second tube-holding inlet attached to said anterior end of said second suction tube, for simultaneously connecting said suction tubes with a conventional operatory suction system.

3. The dental device of claim 1 wherein said Y-tube adapter further comprises a high-volume attachment; and a low-volume attachment secured to said high-volume attachment, for allowing connection of said Y-tube adapter with said conventional operatory suction system.

4. The dental device of claim 1 further comprising a stabilizing shelf secured to said internal surface of said tongue shield, for stabilizing the vertical position of said tongue shield about the tongue.

5. A method for removing saliva from an oral cavity having a tongue, cheek, and teeth, and for retracting the tongue and cheek away from the molar teeth, comprising the steps of:

(a) retracting the tongue away from the teeth within said oral cavity with a generally U-shaped tongue shield having an internal surface, an external surface, a first rear end, and a second rear end;

(b) stabilizing said tongue shield with a bite handle connected to said tongue shield generally forward of said first rear end, said handle being engaged between the teeth when positioned within said oral cavity;

(c) removing saliva with at least one suction tube having a tube wall, from along a structural position of a tube holder secured to said tongue shield approximately adjacent to said first rear end, said tube holder located generally rearward to a rearmost molar tooth when positioned within said oral cavity; and (d) retracting the cheek from the teeth with said at least one suction tube, said tube wall of said at least one suction tube carrying a reinforcement for providing said at least one tube with sufficient sturdiness to retract the cheek from the teeth.

6. The method of claim 5 further comprising the step of propping open the teeth with said bite handle, for allowing greater access to said teeth.

7. A dental device for removing saliva from an oral cavity having a cheek, tongue, and teeth, for increasing access to the teeth by propping open the teeth, and for retracting the tongue and cheek away from the teeth, comprising:

(a) a retraction unit further comprising:

(i) a generally U-shaped tongue shield having an internal surface, an external surface, a first rear end, and a second rear end, for providing a wall between the tongue and the teeth, and for locating the tongue in a retracted tongue position;

(ii) a bite handle connected to said tongue shield in a position forward of said first rear end, projecting outward from said shield, and engaged by the teeth when positioned within the oral cavity, for stabilizing said tongue shield against the tongue, and for propping open the teeth;

(iii) at least one tube holder secured to said tongue shield generally adjacent to said first rear end, projecting outward from said tongue shield, and located generally rearward to a rearmost molar tooth when positioned within said oral cavity;

(b) a suction tube having a tube wall, connected to said tube holder, for removing saliva from along a structural position of said tube holder, and for retracting the cheek from the teeth; and (c) a reinforcement carried within said tube wall of said suction tube, for providing said tube with sufficient sturdiness to retract the cheek from the teeth.

8. The dental device of claim 7 wherein said bite handle is removable and reattachable, for allowing a variable bite handle position.

9. The dental device of claim 7 wherein said tongue shield further comprises a plurality of detachable and reattachable tongue-shield subunits, for allowing more efficient packaging and shipping.

10. The dental device of claim 7 further comprising a cheek retractor means secured to said retraction unit, for aiding said suction tube in retracting the cheek of said oral cavity away from the teeth.

11. The dental device of claim 7 wherein said reinforcement is a ductile wire, for allowing adjustment of the lengthwise shape of said suction tube.

12. The dental device of claim 7 wherein said reinforcement and said suction tube are composed of a sturdy plastic material.

13. The dental device of claim 7 wherein said tube holder attaches within a tube lumen of said suction tube.

14. The dental device of claim 7 wherein said tube holder attaches to the external surface of said suction tube.

15. The dental device of claim 7 wherein said bite handle has a plurality of notches on at least one surface of said handle, for providing a stable engagement of said handle between the teeth when positioned within said oral cavity.

16. The dental device of claim 7 wherein said tongue shield is asymmetrical in shape, said first rear end located further rearward than said second rear end when positioned within the oral cavity, for allowing retraction of mainly one side of the tongue from the teeth.

17. The dental device of claim 7 wherein said tongue shield has a generally symmetrical structure, for retracting both sides of the tongue from the teeth.

18. The dental device of claim 7 wherein said bite handle is engaged between the biting posterior teeth when said device is positioned within said oral cavity.

19. The dental device of claim 7 wherein said bite handle is engaged between the biting anterior teeth when said device is positioned within said oral cavity.

20. The dental device of claim 7 wherein said tube holder further comprises an extension arm secured to said tongue shield generally adjacent to one of said pair of rear ends, for positioning said suction tube further laterally, away from the teeth.

* * * * *